US005093268A

United States Patent [19]

Leventis et al.

[11] Patent Number: 5,093,268
[45] Date of Patent: Mar. 3, 1992

[54] APPARATUS FOR CONDUCTING A PLURALITY OF SIMULTANEOUS MEASUREMENTS OF ELECTROCHEMILUMINESCENT PHENOMENA

[75] Inventors: Nicholas Leventis, Boston, Mass.; Susan E. Morris, Silver Spring, Md.

[73] Assignee: IGEN, Inc., Rockville, Md.

[21] Appl. No.: 647,687

[22] Filed: Jan. 28, 1991

Related U.S. Application Data

[63] Continuation of Ser. No. 187,095, Apr. 28, 1988, abandoned.

[51] Int. Cl.$^5$ .............................. G01N 21/66
[52] U.S. Cl. ...................... 436/172; 250/361 C; 250/362; 250/484.1; 250/459.1; 422/52; 422/68.1; 422/82.07; 422/82.08
[58] Field of Search ............ 422/52, 68.1, 82.07, 422/82.08; 436/172; 250/361 C, 362, 484.1, 459.1

[56] References Cited

U.S. PATENT DOCUMENTS

| 4,236,895 | 12/1980 | Stahl | 436/172 |
| 4,280,815 | 7/1981 | Oberhardt et al. | 422/68 |
| 4,431,919 | 2/1984 | Köstlin et al. | 422/52 |

FOREIGN PATENT DOCUMENTS

WO86/2734  5/1986  World Int. Prop. O.

OTHER PUBLICATIONS

Y. Ikariyama et al., Biochem. Biophy. Reasearch Comm., vol. 128, No. 2, pp. 987-992, Apr. 30, 1985.

Primary Examiner—Timothy M. McMahon
Attorney, Agent, or Firm—Curtis Morris & Safford

[57] ABSTRACT

An apparatus for conducting two or more simultaneous measurements of electrochemiluminescent (ECL) phenomena includes a cell in which a sample including an ECL moiety may be induced to repeatedly emit light in response to electrochemical energy applied by, for example, a working voltammetric electrode. Two or more light detectors such as photomultiplier tubes receive the emitted light at respective wavelengths indicative of respective analytes of interest in the sample.

21 Claims, 6 Drawing Sheets

FIG. 3
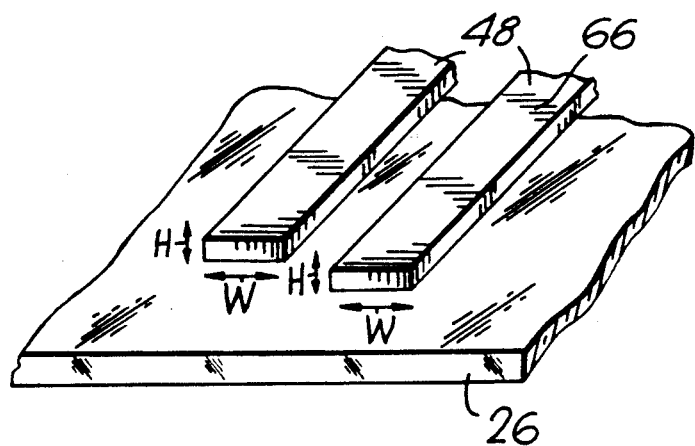
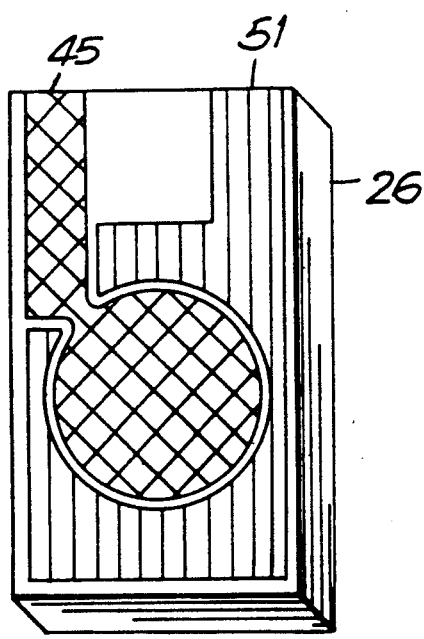
FIG. 4A
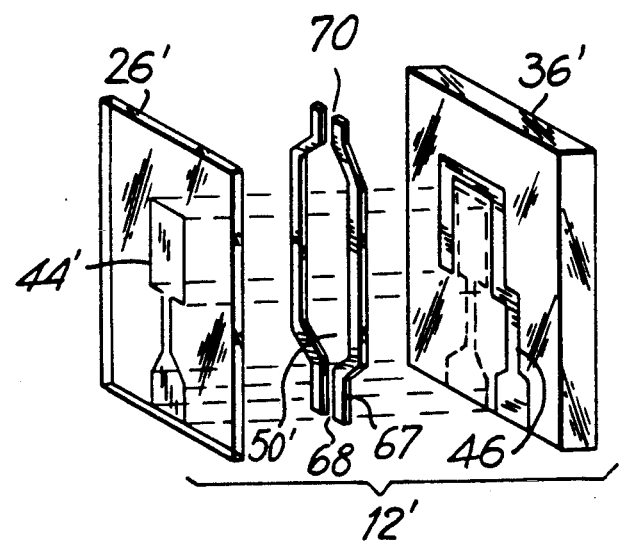
FIG. 5

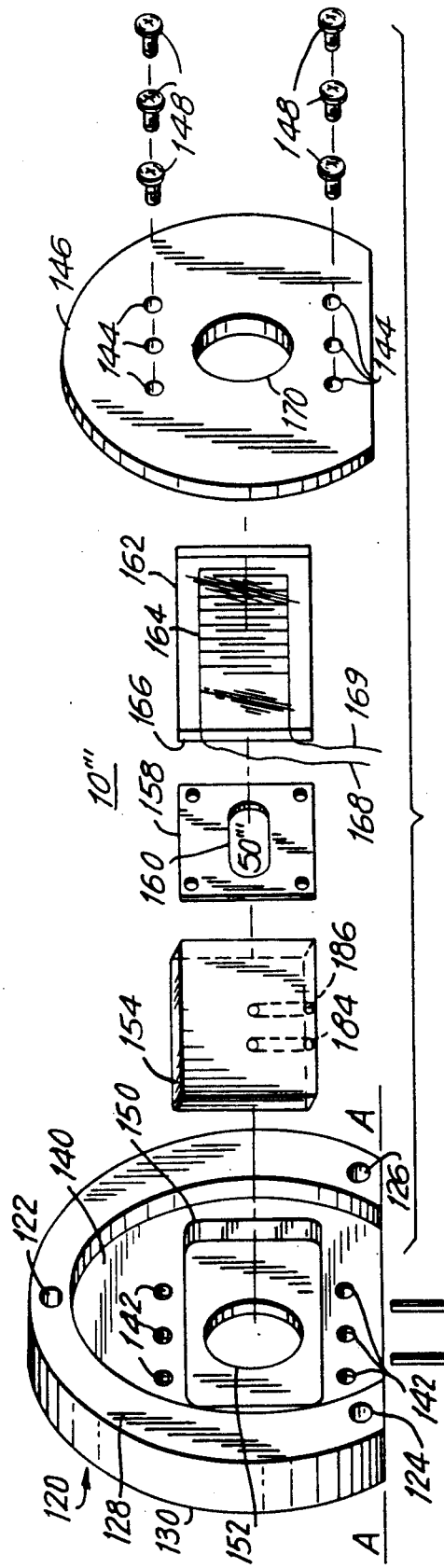
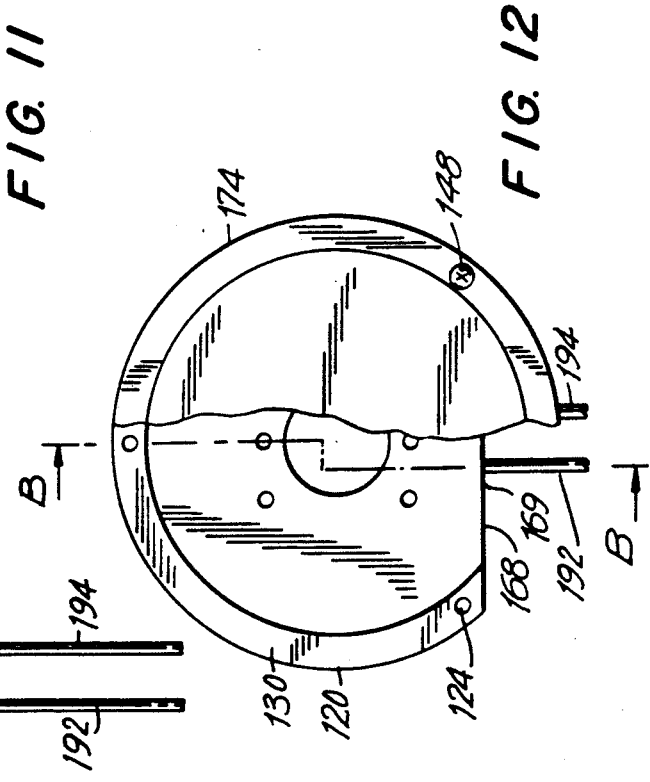
FIG. 11
FIG. 12

APPARATUS FOR CONDUCTING A PLURALITY OF SIMULTANEOUS MEASUREMENTS OF ELECTROCHEMILUMINESCENT PHENOMENA

This application is a continuation of application Ser. No. 187,095, filed Apr. 28, 1988 now abandoned.

FIELD OF THE INVENTION

The present invention relates to electrochemiluminescent phenomena and more particularly relates to the structure and operation of apparatus for conducting measurements of electrochemiluminescent phenomena.

BACKGROUND OF THE INVENTION

Electrochemiluminescent measurement techniques derive from electrochemistry and chemiluminescent detection techniques. Electrochemistry (EC) deals generally with the relation of electricity to chemical changes and with the interconversion of chemical and electrical energy. Chemiluminescence (CL) based assay or detection techniques include, for example, binding assay techniques which generally comprise forming a mixture of a sample containing an unknown amount of an analyte of interest to be determined with a known amount of a reactant which is conjugated with a chemiluminescent label. The mixture is incubated to allow the labeled reactant to bind to the analyte. After incubation, the mixture is separated into two fractions: a bound and an unbound fraction. The bound fraction is labeled reactant bound to analyte and the unbound fraction is the remaining unbound reactant. The CL measurement is then taken. The fractions are chemically caused to luminesce, for example by the addition of an oxidant to the fractions. The bound and unbound fractions of the labeled reactant will emit different amounts of light. The measured level of chemiluminescence at the specific wavelength is indicative of the amount of the bound and/or unbound fraction, respectively and from such measurements one skilled in the art can determine the amount of analyte in the sample.

Electrochemiluminescent (ECL) detection techniques provide a sensitive and controllable measurement of the presence and amount of an analyte of interest. In ECL techniques, the incubated sample is exposed to a voltammetric working electrode, that is, an electrode to which a voltage is applied and from which a current for a redox reaction may be passed. The ECL mixture does not react with the chemical environment alone, as does the CL mixture, nor with an electric field alone as in EC, but rather electrochemiluminescence is triggered by a voltage impressed on the working electrode at a particular time and in a particular manner to controllably cause the ECL moiety to emit light at the electrochemiluminescent wavelength of interest. The voltage impressed on the working electrode generates the oxidant in situ which, in the CL methodology, is added externally.

The reverse side of this sensitivity is that, in general, a particular sample of the reactive mixture may not be measurable twice to produce exactly the same result, although sometimes the results may be close enough to be considered the same. The ECL measurement is destructive, in that the sample changes its chemical composition during the measurement. In accordance with a proposal by employees of the assignee of the present application who are under an obligation of assignment to the present assignee, the working electrode may be conditioned to provide a precisely controlled surface for subsequent ECL measurements. This provides controllable initial conditions for each individual sample in succession, but the conditions change after measurement.

It has further been proposed by another employee of the present assignee also under an obligation of assignment thereto to provide an internal standard ECL measurement, in which a known amount of labeled reactant is present in the reactive mixture to provide a calibrating signal against which to measure the electrochemiluminescence of the analyte of interest. The internal standard is therefore a second analyte of interest which can emit light at a second, different wavelength. Advantageously the internal standard will have the same chemical mechanism for chemiluminescence as the prime analyte of interest and differ only in the wavelength of its emitted light. Alternatively, a second analyte of interest which is not an internal standard may be present in the reactive mixture. Since the second analyte also emits light when triggered by the voltage impressed on the working electrode, its electrochemiluminescence will also be affected by the irreversible chemical changes during the ECL measurement process. It would be highly advantageous to measure the levels of electrochemiluminescence of the prime analyte of interest and the internal standard (or second analyte of interest) simultaneously before the response of either one is destroyed or reduced during the ECL measurement of the other.

It is known in some CL light measurements (which do not use electrodes for triggering a reaction) to measure light intensities at two different wavelengths for the same analyte to provide an intrinsic improvement in precision since some variations in the signal cancel. Two separate phototubes may be used for this purpose, with an appropriate filter for each, or a single phototube with rotating filters may alternatively be used. In the case of using two phototubes, there is no restriction in the spatial placement of these phototubes since the light is generated in the bulk of the CL solution, with the result that it is emitted uniformly in all directions.

The problem faced in ECL techniques, as discussed more fully below, is a different problem altogether which relates to the fact that light is produced as a result of chemical changes happening in a layer of sample immediately surrounding the electrode surface, due to the electrical potential imposed on the electrode. A technique which would preserve the chemical integrity of this layer for the two measurements would provide a more accurate measurement of the concentration of the two analytes.

Another difficulty in the measurement of light at two electrochemiluminescent wavelengths arises from the fact that the electrode by its nature prevents light from being emitted uniformly in all directions. This imposes geometric restrictions on the method to be used for the simultaneous measurement of the light that originates from the primary analyte and the light that originates from the internal standard.

OBJECTS AND SUMMARY OF THE INVENTION

It is therefore an object of the present invention to provide apparatus and a method for conducting measurements of electrochemiluminescent phenomena which avoid the above-described difficulties of the prior art.

It is a further object of the present invention to provide apparatus and a method for conducting measurements of electrochemiluminescent phenomena which provide a more accurate measurement of two or more analytes of interest present in the same sample fluid.

It is a further object of the present invention to provide apparatus and a method for conducting at least two simultaneous measurements of electrochemiluminescent phenomena on respective analytes of interest present in the same sample fluid.

It is yet a further object of the present invention to provide an apparatus which can be operated to conduct measurements of electrochemiluminescent phenomena of two or more analytes of interest without destroying any analyte of interest prior to measurement of the other analytes of interest.

It is a further object of the present invention to provide apparatus and a method for conducting two or more simultaneous measurements of electrochemiluminescent phenomena which maximize the amount of light available for all these simultaneous measurements.

It is yet a further object of the present invention to provide apparatus and a method for conducting two simultaneous measurements of electrochemiluminescent phenomena in which light is directed towards two or more sides of a sample holding cell, whereby separate light detectors may be positioned at the separate sides for detection of light at respective electrochemiluminescent wavelengths.

It is a further object of the present invention to provide an apparatus and a method for conducting two or more simultaneous measurements of electrochemiluminescent phenomena with the minimum sample volume.

These and other objects, aspects and features of the present invention will be apparent from the following detailed description of the preferred embodiments taken in connection with the accompanying drawings, throughout which like reference numerals denote like elements and parts.

BRIEF DESCRIPTION OF THE DRAWINGS

FIG. 3 is a side perspective view of two electrode strips used in the apparatus of FIG. 1;

FIG. 4A is a plan view of an alternative electrode structure for the apparatus of FIG. 1;

FIG. 5 is a schematic view of a structure of a flow-through cell;

FIG. 11 is an exploded side perspective view of a third embodiment of the apparatus according to the present invention;

FIG. 12 is an assembled elevational view, partly in cross section, of the apparatus of FIG. 11 together with a photomultiplier tube device assembled therewith;

DETAILED DESCRIPTION OF THE PREFERRED EMBODIMENTS

Figure 1:
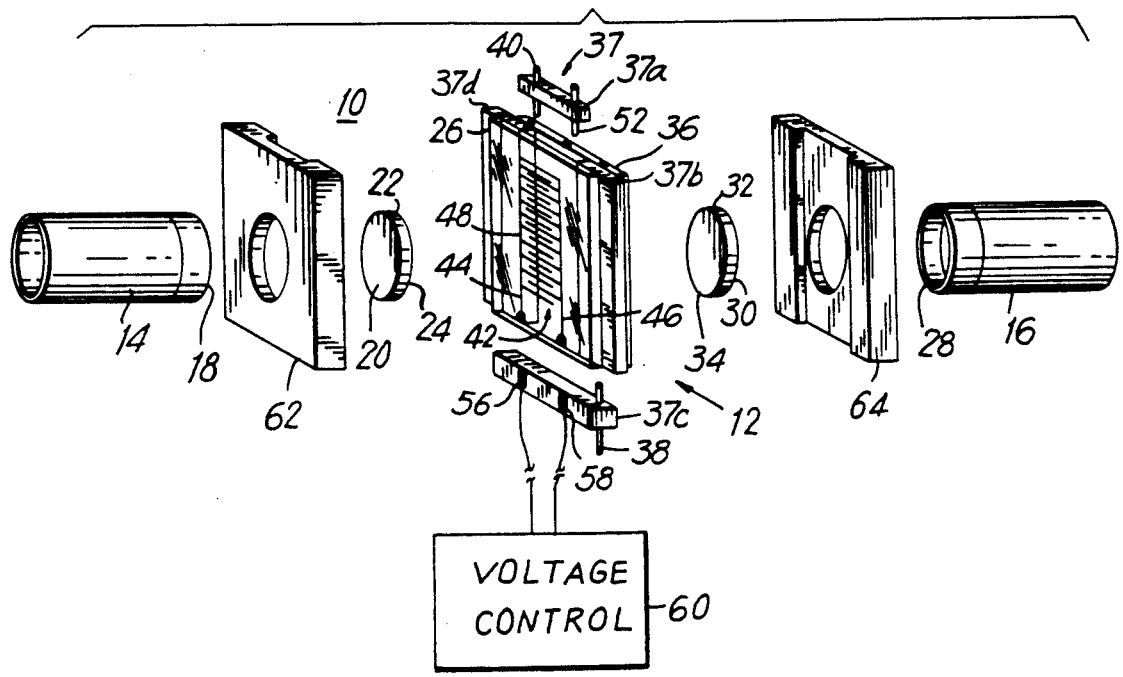
FIG. 1 is an exploded side perspective view of a first embodiment of the apparatus according to the present invention.

The present invention relates to apparatus and the operation of such apparatus for performing measurements of ECL phenomena and in particular is directed to apparatus which permits the simultaneous measurement of light at two or more electrochemiluminescent wavelengths. As background for understanding this invention, it is believed that a brief description of the ECL phenomena themselves is appropriate.

The ECL technique developed by employees of the assignee of the present application and under an obligation of assignment thereto is a method of detecting in a volume of a multicomponent, liquid sample an analyte of interest present in the sample in relatively small concentrations and which comprises: a) contacting a sample with a reagent (i) capable of being induced to repeatedly emit electromagnetic radiation upon exposure to an amount of electrochemical energy from a suitable source effective to induce the reagent to repeatedly emit radiation and (ii) capable of combining with the analyte of interest, the contact being effected under appropriate conditions such that the analyte and the reagent combine; b) exposing the resulting sample to an amount of electrochemical energy from a suitable source effective to induce the reagent to repeatedly emit radiation, the exposure being effected under suitable condition so as to induce the reagent to repeatedly emit electromagnetic radiation; and c) detecting electromagnetic radiation so emitted and thereby detecting the presence of the analyte of interest in the sample.

The methods provided in this ECL technique may be performed in heterogeneous assays, i.e. assays in which unbound labeled reagent is separated from bound labeled reagent prior to exposure of the bound or unbound label reagent to electrochemical energy, and in homogeneous assays, i.e. assays in which unbound labeled reagent and bound labeled reagent are exposed to electrochemical energy together. In homogeneous assays the intensity of the electromagnetic radiation (light) emitted by the bound labeled reagent is either greater than or less than the intensity of electromagnetic radiation (light) emitted by the unbound labeled reagent. The presence or absence of the respective bound and unbound components can be determined by measuring the difference in intensity.

In one such ECL technique, any reagent which is not combined with the analyte of interest is separated from the sample which had been contacted with the reagent prior to exposure of the sample to electrochemical energy. In another technique, prior to contacting the sample with the reagent, the sample is treated so as to immobilize the analyte of interest. Means for immobilizing analytes of interest are well known in the art and include contacting the sample with a particular surface.

The ECL techniques may be used in a variety of detection and quantitative assay formats as are well known in the art. In quantitative assays a known amount of ECL reagent is used and the amount of electrochemiluminescence measured is correlated to known standards to calculate the amount of analyte present. Forward, reverse, competitive and sandwich assays can be performed by methods well known to the skilled worker. In competitive assays, for example, a method for quantitatively determining the amount of an analyte of interest in a volume of a multicomponent, liquid sample is performed as follows. The sample is contacted with a known amount of an electrochemiluminescent reagent which is capable of competing with the analyte of interest for binding sites on a complementary material not normally present in the sample and with a known amount of the complementary material, the contact being effected under appropriate conditions such that the analyte of interest and the reagent competitively bind to the complementary material. The resulting sample is exposed to electrochemical energy and the amount of radiation emitted is quantitatively determined, thereby quantitatively determining the amount of the analyte of interest present in the sample.

The analyte of interest may be, for example, a whole cell, subcellular particle, virus, prion, viroid, nucleic acid, protein, lipoprotein, lipopolysaccharide, glycoprotein, peptide, hormone, pharmacological agent, non-biological polymer, synthetic organic molecule, organometallic molecule or an inorganic molecule present in the sample. Moreover the analyte of interest may be a whole cell, subcellular particle, virus, prion, viroid or nucleic acid present in the sample.

The sample may be derived from, for example, a solid, emulsion, suspension, liquid or gas. Furthermore, the sample may be derived from, for example, water, food, blood, serum, plasma, urine, feces, tissue, saliva, oils, organic solvents or air. Moreover, the sample may comprise, for example, acetonitrile, dimethyl sulfoxide, dimethyl formamide, n-methyl-pyrrolidinone or tert-butyl alcohol. The sample may comprise a reducing agent or an oxidizing agent.

The reagent which is contacted with the sample may comprise, for example, an electrochemiluminescent chemical moiety conjugated to a whole cell, subcellular particle, virus, prion, viroid, lipid, fatty acid, nucleic acid, polysaccharide, protein, lipoprotein, lipopolysaccharide, glycoprotein, peptide, cellular metabolyte, hormone, pharmacological agent, tranquilizer, barbituate, alkaloid, steroid, vitamin, amino acid, sugar, non-biological polymer, synthetic organic molecule, organo metallic molecule, inorganic molecule, biotin, avidin or streptavidin. In one example, the agent is an electrochemiluminescent moiety conjugated to an antibody antigen, nucleic acid, hapten, ligand or enzyme, or biotin, avidin or streptavidin. The reagent may be the analyte of interest conjugated to an electrochemiluminescent chemical moiety or an analog of the analyte of interest conjugated to an electrochemiluminescent moiety.

The electrochemiluminescent chemical moiety may comprise, for example, a metal-containing organic compound wherein the metal is selected from the group consisting of ruthenium, osmium, rhenium, irridium, rhodium, platinum, palladium, molybdenum, technetium and tungsten.

The above discussion illustrates the broad applicability of ECL measurement techniques to many different analytes of interest and the different methods and assays for qualitatively and quantitatively detecting their presence in the multicomponent, liquid sample. For a fuller description of these ECL techniques, reference should be made to PCT Patent Application No. US87/00987, assigned in common with the present application.

As noted above, these ECL techniques may include the detection of a multiplicity, that is, two or more, analytes of interest in the same sample. When the ECL measurements are being quantitatively performed, the measurement should be as precise and as accurate as possible. The precision of the measurement refers to its repeatability, that is, the extent to which a measurement with the same initial conditions and the same chemical composition of sample will produce the same result. The accuracy refers to the closeness of the measured concentration to the actual concentration. In order to enhance the precision of such ECL measurements, it has been proposed by employees of the present assignee having an obligation of assignment thereto to condition the electrode supplying the electrochemical energy in a highly repeatable manner to produce a specific surface on the electrode. This means that if a particular sample is supplied for measurement, the result will be repeatable within a certain percent, for example, of relative standard deviation.

The present invention is directed to a different aspect of apparatus for conducting ECL measurements: the accuracy of the measurement. Each ECL measurement is taken by exposing the sample to the electrode system of the apparatus, more particularly to the voltammetric working electrode thereof, and impressing a known, variable voltage on the working electrode so as to trigger electrochemiluminesence. This known voltage is frequently in the form of a voltage sweep from a first voltage to a second voltage, back through first voltage to a third voltage and then back again to the first voltage. The nature of the ECL reaction is such that the samples will chemically change during the ECL measurement process. Not only does the sample chemically change from voltage sweep to voltage sweep, but it also can change significantly during a single voltage sweep. Therefore, it may happen that the chemical constitution of the sample at the start of the first ECL sweep is unique and is destroyed by that first ECL sweep. During each subsequent ECL sweep or portion thereof, the chemical constitution of the sample is not the same as its original chemical constitution.

The qualitative nature of the chemical change in the sample is believed to be as follows. The electrochemiluminescent moiety, termed a TAG in the above-referenced and commonly assigned application, may or may not be bound to an analyte, but in either case it may be promoted to an excited state as a result of a series of chemical reactions triggered by the electrical energy received from the working electrode. For example, a TAG may be oxidized from a 2+ to a 3+ oxidation state in the following reaction that happens at the working electrode:

$$TAG^{2+} \rightarrow TAG^{3+} + e^- \qquad (1)$$

This reaction is known to take place only in the thin layer of sample fluid immediately touching the electrode surface (diffusion layer).

The oxidized TAG ($TAG^{3+}$) will luminesce if it can react with a strong reductant $P^o$ which is able to reduce $TAG^{3+}$ back to $TAG^{2+}$, but in an electronically excited state. This molecule, in a prefered embodiment as described in the U.S. patent application Ser. No. 06/858,354, is provided by mixing the TAG in a buffer solution with a high concentration of a precursor P, which may advantageously be oxalate. The energy from the electrode causes first the oxidation of the precursor P as follows:

$$P \rightarrow P^+ + e^- \quad (2)$$

Then the oxidized precursor (P+) can rearrange unimolecularly to give the strong reductant $P^o$:

$$P^+ \rightarrow P^o \quad (3).$$

The reactions of equations (1), (2) and (3) all occur during a portion of the measurement sweep when the voltage at the working electrode reaches a triggering value. Now the $TAG^{3+}$ reacts chemically with the reductant $P^o$ to yield $TAG^{2+}$ in an electronically excited state denoted with an asterisk (*) as follows:

$$TAG^{3+} + P^o \rightarrow TAG^{2+*} + P_D \quad (4)$$

wherein $P_D$ is a modified form of the precursor which is not reactive as in equation (2). The excited $TAG^{2+*}$ now luminesces, that is, it emits light as follows:

$$TAG^{2+*} \rightarrow TAG^{2+} + hc/\lambda \quad (5)$$

where h is Planck's constant, c is the speed of light and $\lambda$ is the wavelength of the emitted light.

Thus, in the course of a measurement sweep, the $TAG^{2+}$ is oxidized, then chemically reacts to reach an excited state and finally luminesces and returns to its original condition, except for any part thereof which fails to get oxidized or to contact a reductant molecule. However, the precursor P is not returned to its reactive state, but rather is chemically changed to its non-reactive state $P_D$. As noted above, only the TAG molecules in a thin layer surrounding the working electrode react during a potential sweep, and after a sweep each TAG molecule is next to an inert precursor molecule $P_D$. While some active precursor P remains in the layer, there is the clear possibility that during the next measurement sweep less P will be available to get oxidized to give $P^+$ that eventually yields $P^o$ and some of the TAG will not find a reductant $P^o$ to react with, so that the intensity of light, which is proportional to the number of TAG molecules luminescing, will be decreased. Since, however, it is the light intensity which is used as a measure of the concentration of the analyte, the accuracy of the measurement is impaired.

However, the quantitative nature of this chemical change is unknown, and therefore to compare the data taken in two different sweeps, it is generally assumed that the chemical constituents are the same. The false assumption of constant chemical constitution will be reflected in erroneously interpreted results. That is, the results from two different sweeps will differ, not because the sweeps are inaccurate but because the composition and the concentration of the chemicals that are involved in the measurement have changed. In the absence of knowing how they have changed, however, even a slight difference in result is factored into a measured concentration, which will therefore be inaccurate.

This problem needs to be overcome when an internal standard is used. In such a situation, the internal standard constitutes a second analyte of interest which is to be detected in the same sample containing the prime analyte of interest and is selected to have a reactive mechanism as close as possible to that of the prime analyte of interest. For a fuller description of an internal standard, reference should be made to pages 100-103 of U.S. patent application Ser. No. 117,017, filed Nov. 4, 1987 and assigned in common with the present application. The disclosure of application Ser. No. 117,017 is incorporated by reference. If the prime analyte of interest is measured in a first sweep and the internal standard is measured in a second sweep, or vice versa, the above problem may lead to difficulties in appropriately measuring of the prime analyte of interest using the internal standard, because the chemical constitution surrounding the internal standard will have been changed by the first measurement sweep. On the other hand, due to the fact that the chemical composition and the light intensity change in a non-linear fashion during the very same linear potential sweep, even if the prime analyte of interest is measured in a first portion of the measurement sweep and the internal standard is measured in a second portion of that first measurement sweep, or even if they are measured alternatively and repeatedly with some kind of alternating sampling, storage and averaging mechanism, the highly sensitive and precise nature of these ECL measurements means that the error due the change in chemical composition during the same potential sweep may not be insignificant. The purpose of the present invention is to eliminate this error by providing apparatus in which two measurements of ECL phenomena may be conducted simultaneously.

Accordingly, the present invention includes in a broad aspect thereof an apparatus for conducting two simultaneous measurements of electrochemiluminescent phenomena. The apparatus comprises electrochemical cell means for holding a sample therein, the cell means including a sample-holding volume and first and second transparent plates at least partly defining the sample-holding volume therebetween, (b) electrode means including at least a working electrode and a counterelectrode for triggering electrochemiluminescence in a sample held within the sample-holding volume, the working electrode being mounted on at least one of the first and second transparent plates so as to be exposable to the sample and further being substantially transparent at a plurality of electrochemiluminescent wavelengths and being configured so as to trigger the sample to emit electrochemiluminescent radiation towards the first and second transparent plates, (c) first light detection means having a light receiving surface confronting the first transparent plate for detecting radiation at a first one of the electrochemiluminescent wavelengths and second light detection means having a light receiving surface confronting the second transparent plate for detecting radiation at a second one of the electrochemiluminescent wavelengths, the first and second light detection means being independently operable and adapted for simultaneous operation for light detection at the first and second wavelengths, respectively.

The first and second transparent plates may be flat and may be opposed to define the sample-holding volume therebetween. Advantageously, the electrode means is configured so as to trigger the sample to emit electrochemiluminescent radiation substantially equally towards the first and second plates. When the counter electrode is substantially transparent, both it and the working electrode may be mounted on the first transparent plate and be formed as a set of spaced, connected electrodes, the two sets of electrodes being interdigitated to form a substantially transparent interdigitated array on the first transparent plate. Advantageously, each of the sets of electrodes is a set of microelectrodes.

Furthermore, each of the first and second light detection means may include a respective filter means at the respective transparent plate, the respective filter means being adapted to transmit light at the respective first and second wavelengths, and detector means for detecting light passed by the respective filter means. The respective filter means may be removable from the apparatus and the light detection means may include photomultiplier tube means. The working electrode may be mounted on the first transparent plate and the counter electrode may be substantially transparent and mounted on the second transparent plate.

The cell means itself may be removable from the apparatus, the apparatus further comprising cell holding means for removably holding the cell means at an operative position in the apparatus and fluid transport means for providing a flow of fluid to and from the cell means at the operative position, the cell means being a selected one of a flow-through cell adapted to transfer fluid from and to the fluid transport means and a disposable cell having a sample fluid contained therein.

The above-described apparatus may more generally be an apparatus for conducting a plurality of simultaneous measurements of electrochemiluminescent phenomena. In such case, a plurality of light detection means having respective light receiving surfaces confronting ones of the first and second transparent plates for detecting light at respective ones of the electrochemiluminescent wavelengths are independently operable and adapted for simultaneous operation for light detection at the respective wavelengths.

Furthermore, in accordance with a broader aspect of the present invention, an apparatus for conducting a plurality of measurements of electrochemiluminescent phenomena comprises (a) electrochemical cell means for holding a sample therein, the cell means including a sample-holding volume, (b) electrode means including at least a working electrode and a counter electrode for triggering electrochemiluminescence in a sample held within the sample-holding volume, the working electrode being mounted in the sample-holding volume so as to be exposable to the sample, (c) first and second light detection means for detecting light at at least first and second electrochemiluminescent wavelengths, respectively and (d) means interposed between the first and second light detection means and the cell means for transmitting light at the first and second electrochemiluminescent wavelengths from the sample to the light detection means.

Advantageously, the first and second light detection means include respective light receiving surfaces and the means for transmitting light includes first and second filter means confronting the respective light receiving surfaces of the first and second light detection means for passing light at the first and second ones of the electrochemiluminescent wavelengths, respectively. The cell means may include a plate which is at least partly transparent and at least one of the filter means may confront the plate to receive light transmitted therethrough.

A specific advantageous apparatus for conducting two simultaneous measurements of electrochemiluminescent phenomena comprises electrochemical cell means for holding a sample therein, the cell means including opposed first and second transparent plates defining a sample-holding volume therebetween, (b) electrode means mounted in the cell means and including at least a working electrode and a counter electrode for triggering electrochemiluminescence in a sample held within the sample-holding volume, the working electrode being mounted on at least one of the first and second transparent plates so as to be exposable to the sample and further being substantially transparent at a plurality of electrochemiluminescent wavelengths and being configured so as to trigger the sample to emit electrochemiluminescent radiation towards the first and second transparent plates, (c) cell holding means for removably holding the cell means at an operative position within the apparatus and (d) voltage control means adapted to be electrically connected to the electrode means when the cell means is held at the operative position for applying voltage signals to the electrode means. The apparatus further comprises (e) first light detection means for detecting light at a first one of the electrochemiluminescent wavelengths, the first light detection means including filter means directly confronting the first transparent plate and adapted to transmit light at the first one of the electrochemiluminescent wavelengths and photomultiplier tube means having a light receiving surface directly confronting the first filter means for detecting light transmitted by the latter, and (f) second light detection means for detecting light at a second one of the electrochemiluminescent wavelengths, the second light detection means including second filter means having a respective light receiving surface directly confronting the second transparent plate for transmitting light at the second one of the electrochemiluminescent wavelengths and second photomultiplier tube means directly confronting the second filter means for receiving light transmitted by the latter, the first and second light detection means being independently operable, whereby the apparatus is adapted for light detection at the first and second wavelengths by the first and second light detection devices, respectively, to conduct two simultaneous measurements of electrochemiluminescent phenomena.

In accordance with the broad aspect of the present invention, a method for conducting a plurality of simultaneous measurements of electrochemiluminescent phenomena comprises the steps of (a) selecting a sample including at least first and second electrochemiluminescent moieties respectively including first and second analytes of interest, the fist analyte of interest being electrochemically inducable to emit light at a first electrochemiluminescent wavelength and said second analyte of interest being electrochemically inducable to emit light at a second electrochemiluminescent wavelength, (b) exposing the sample to a working electrode adapted to induce the emission of light in the sample, (c) applying a voltage signal to the working electrode to induce the emission of light at the first and second electrochemiluminescent wavelengths, (d) detecting light at the first electrochemiluminescent wavelength using a first detection means and (e) simultaneously detecting light at the second electrochemiluminescent wavelengths using a second light detection means.

Turning now to the drawings and initially to FIG. 1 thereof, a first embodiment of the apparatus 10 according to the present invention and adapted to perform two simultaneous measurements of electrochemiluminescent phenomena includes an electrochemical cell 12 and first and second light detectors 14, 16, each of which is advantageously a photomultiplier tube (PMT). Other types of light detectors, for example, photodiodes or CCD devices, may alternatively be used. Further, a photographic film or emulsion may also be used to detect the light. PMT 14 has a light receiving surface 18 which is adapted to directly confront a back surface 20 of a first filter 22. First filter 22 has a front surface 24 which advantageously directly confronts and abuts a first transparent side plate 26 of cell 12. Correspondingly, second PMT 16 has a light receiving surface 28 which directly confronts the back surface 30 of a second filter 32. Second filter 32 has a front surface 34 which directly confronts and advantageously abuts a second transparent side plate 36 of cell 12. First and second transparent plates 26, 36 are opposed to define a sample-holding volume 50 in cell 12 and within which the sample for ECL testing is contained. A spacer 37, advantageously made of Teflon and formed in four sections 37a, b, c and d, is positioned between plates 26 and 36 and has a central opening forming the side walls of the sample-holding volume. Advantageously spacer 37 is relatively thin so as to minimize the volume of sample required to fill it for each measurement. For example, cell 12 might hold approximately 10–20 microliters of sample at any one time.

In this first embodiment, cell 12 is a so-called flow-through cell in which the sample is introduced through an inlet pipe 38 and removed through an outlet pipe 40. Both inlet and outlet pipes 38, 40 are advantageously formed of stainless steel.

First filter 22 is adapted to transmit light at a first selected electrochemiluminescent wavelength λ1. First transparent plate 26 therefore need not necessarily be transparent at all light wavelengths, but should be substantially transparent at first wavelength λ1. Correspondingly, second filter 32 transmits light at a second electrochemiluminescent wavelengths λ2, and second plate 36 should be transparent at least at second wavelength λ2. First and second wavelengths λ1, λ2 are selected to correspond to the wavelengths which are anticipated to be produced by the two analytes of interest held within the multicomponent sample. If apparatus 10 is to be dedicated to a single type of assay which will always look for the two specific wavelengths λ1, λ2 from two predetermined analytes of interest, filters 22 and 32 may be permanently installed in apparatus 10. Alternatively and advantageously, if apparatus 10 is intended to be adaptable for ECL measurements at different wavelengths for different analytes of interest, filters 22 and 32 may be removable and therefore replaceable with other filters for selecting other wavelengths. For proper discrimination, filter 22 will not transmit light at second wavelength λ2, while second filter 32 will not transmit light at first wavelength λ1.

Figure 2:
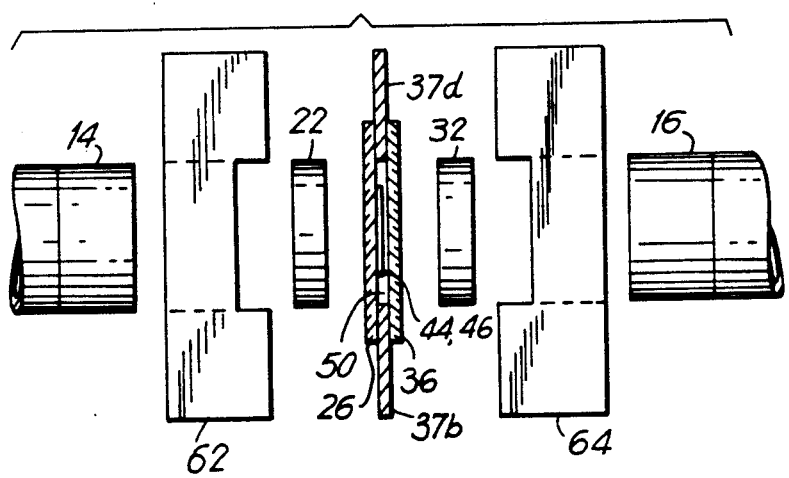
FIG. 2 is an exploded top plan view of the apparatus of FIG. 1.

An electrode system 42 is provided for supplying the electrical component of the electrochemical energy used to trigger the ECL reaction. In accordance with the present invention, light at two ECL wavelengths λ1, λ2 is to be received both at first plate 26 and and second plate 36, respectively. Cell 12 and electrode system 42 are both configured so that the triggered sample will emit light towards both first and second plates 26 and 36. To this end, cell 12 is of the shape described above, that is, narrow with opposed first and second plates 26, 36 directly confronted by filters 22, 32 respectively passing light at the selected wavelengths to PMTs 14, 16. In a preferred embodiment of the electrode system 42, a working electrode 44 and a counter electrode 46 are each a set of spaced, connected electrode strips 48, the two sets of electrode strips being interdigitated to form an interdigitated array on the interior surface of the first plate 26. As shown in FIG. 2, this interdigitated array of working electrode 44 and counter electrode 46 may be provided on the interior surface of one of first or second plates 26, 36 so as to be exposed to any sample held within sample-holding volume 50. Cell 12 advantageously also includes a reference electrode 52 extending through top spacer section 37d of cell 12 into sample-holding volume 50. Alternatively, reference electrode 52 could be mounted upstream, before the inlet pipe 38 or downstream, after the outlet pipe 40.

In addition, electrode system 42 includes first and second connecting electrodes 56, 58 mounted on bottom spacer portion 37c and which are adapted to make electrical contact with working electrode 44 and counter electrode 46, respectively, when apparatus 10 is assembled. Connecting electrodes 56, 58 supply selected voltage signals from a voltage control 60, which advantageously operates in the manner of a potentiostat to supply the voltage signals to working and counter electrodes 44, 46 and to measure the currents flowing through the respective electrodes. In a two electrode mode of operation, reference electrode 52 does not receive a separate voltage signal. However, in a three electrode mode of operation, voltage control 60 is connected through another connecting electrode (not illustrated) to the reference electrode 52.

Working electrode 44, or more specifically the thin layer of sample touching working electrode 44, is where the electrochemical reaction of interest occurs. In ECL applications, working electrode 44 is a solid voltammetric electrode, advantageously constructed of platinum, gold, carbon or other materials which are effective for this purpose. Counter electrode 46 is also a solid electrode advantageously constructed of platinum, gold, stainless steel or other materials, and completes the electrochemical cell. During the ECL measurement process, other electrochemical reactions take place at counter electrode 46, but they are not the type to stimulate the emission of electrochemiluminesence and therefore need not be considered here. Reference electrode 52 provides a reference voltage to which the voltage applied by the working electrode 46 is referred, for example, +1.2 volts versus the reference. When reference electrode 52 provides a known, poised and stable voltage, it is advantageously constructed of silver/silver chloride (Ag/AgCl) or is a saturated calomel electrode (SCE). Reference electrode 52 may alternatively be a so-called "quasi reference" electrode, constructed of platinum, gold, stainless steel or other material, the potential of which is unknown, but constant, and against which the voltage applied to working electrode 44 is measured. In the two electrode mode of operation, reference electrode 52 does not function separately from counter electrode 46 but rather may be electrically connected thereto. In this case, voltage control 60 operates essentially as a battery. In the three electrode mode, current does not flow through the reference electrode 52.

Voltage control 60 in its potentiostat operation controls electrode system 42 by providing a known voltage at working electrode 44 with respect to reference electrode 52 while measuring the current flow between working electrode 44 and counter electrode 46. Potentiostats for this purpose are well known, and the internal structure of voltage control 60 may therefore correspond to any of the conventional potentiostats which produce the above-recited functions and so does not form a part of the present invention per se. Indeed apparatus 10 may alternatively be constructed without an internal voltage control 60, but rather may be adapted to be connected to a conventional potentiostat which is separately controlled for providing the required voltage signals to electrodes 44, 46 and 52. Advantageously, however, voltage control 60 may be programmed, for example through microprocessor control, to apply the appropriate voltage signals automatically in a preselected sequence.

Therefore, when a sample containing two analytes of interest is introduced through inlet pipe 38 into sample holding volume 50 within cell 12 and the voltage control 60 is connected to working electrode 44 and to counter electrode 46 (and optionally to the reference electrode 52), light at the two wavelengths λ1, λ2 will be triggered in the portion of the sample surrounding working electrode 44 and, by the construction of cell 12 and advantageously the construction of working electrode 44, as discussed below, will be transmitted both towards first plate 26 and towards second plate 36. First filter 22 will transmit only the light at first wavelength λ1 to first PMT 14, which will detect the intensity of the light generated and hence the concentration of the first analyte of interest in the sample. Corresponding, second filter 32 will transmit only the light at second wavelength λ2 to second PMT 16, which will detect the intensity of light at wavelength λ2 and hence the concentration of the second analyte of interest in the sample.

In the apparatus 10 as assembled, first PMT 14 and first filter 22 are mounted with confronting surfaces in contact and directly confronting first plate 26 by a first mounting block 62. Correspondingly, second PMT 16 and second filter 32 are mounted with confronting surfaces in contact and directly confronting second plate 36 by a second mounting block 64. This eliminates any need for optical elements to transmit the light from cell 12 to filters 22, 32, and so maximizes the light available for detection. This arrangement in apparatus 10 also insures that PMT 14 receives light only at the first wavelength λ1 through filter 22 and does not receive any light at wavelength λ2 which may be transmitted through second plate 36 and in some way reflected back toward PMT 14. Correspondingly, PMT 16 similarly receives light only at the second wavelength λ2 through filter 32 and does not receive any light at the first wavelength λ1 emitted through the first plate 26 and in any matter reflected back. Furthermore, the entire apparatus is contained within a lightproof housing (not illustrated) so that no external light will be received by either PMT 14 or 16.

Alternatively, however, optical elements such as optical fibers may be used to transmit light from cell 12 to a filter/PMT arrangement spaced therefrom.

One of the advantages, though, of the head-to-head arrangement of two PMTs 14, 16 is that each PMT 14,16 with its respective filter 22, 32 can be mounted directly onto the respective plates 26, 36 without any "dead" space between the light receiving surfaces 18, 28 of the two PMTs 14, 16 and cell 12. This first prevents any scattered light from entering PMTs 14, 16 and, as noted above, eliminates the need for any optics for light collection and direction. Such optics are necessary if the cell plates 26, 36 are not transparent. Another advantage of this particular embodiment is that it does not employ any moving parts, such as light choppers or filter wheels. Such moving parts tend to break down and are to be avoided in any apparatus which is desirably maintenance-free. Such parts may, however, be used in other embodiments. Another advantage yet is that the two facing plates 26 and 36 can be spaced by spacer 37 as close as possible by making the spacer as thin as possible, with the result that sample-holding volume 50 is small and requires only a small amount of sample for the assay.

The interdigitated array of working electrode 44 and counter electrode 46 is an advantageous construction for electrode system 42 in that it permits a significant amount of light generated by the electrochemical reaction to be transmitted through each transparent plate 26, 36. As shown in FIG. 3, each of the individual electrodes 48 making up working electrode 44 and counter electrode 46 is formed as a narrow rectangular strip having a height H and width W. The ECL reaction takes place in that volume of the sample fluid which directly surrounds and coats working electrode 44 and does not occur in significant amounts in the remaining portion of the sample. Electrode strips 48 are mounted on the interior surface of first plate 26 and therefore are exposed to the sample only along their respective side surfaces of height H and one top surface 66, the bottom surface of each electrode strip 48 being protected from exposure by plate 26. If height H were relatively small and width W were relatively large, then the majority of the surface area at which the electrochemical reaction takes place would be on the top surfaces 66, and light generated thereat could not pass through electrode strips 48 to first plate 26 and thence to PMT 14, but rather would be transmitted substantially in its entirety away from first plate 26 and towards second plate 36. However, if width W is made relatively small, so that in the limit electrode strips 48 become microelectrodes, then a large percentage of the light will be emitted from the side surfaces of electrode strips 48 and will be transmitted equally through first plate 26 and second plate 36. Ideally, light should be directed substantially equally towards both plates 26, 36, but the mounting of working electrode 44 on either plate 26, 36 will inevitably block some of the light triggered by that working electrode. It is, of course, possible to mount a second working electrode on the second plate 36 as long as suitable means provide the appropriate voltage signals thereto.

Figure 4B:
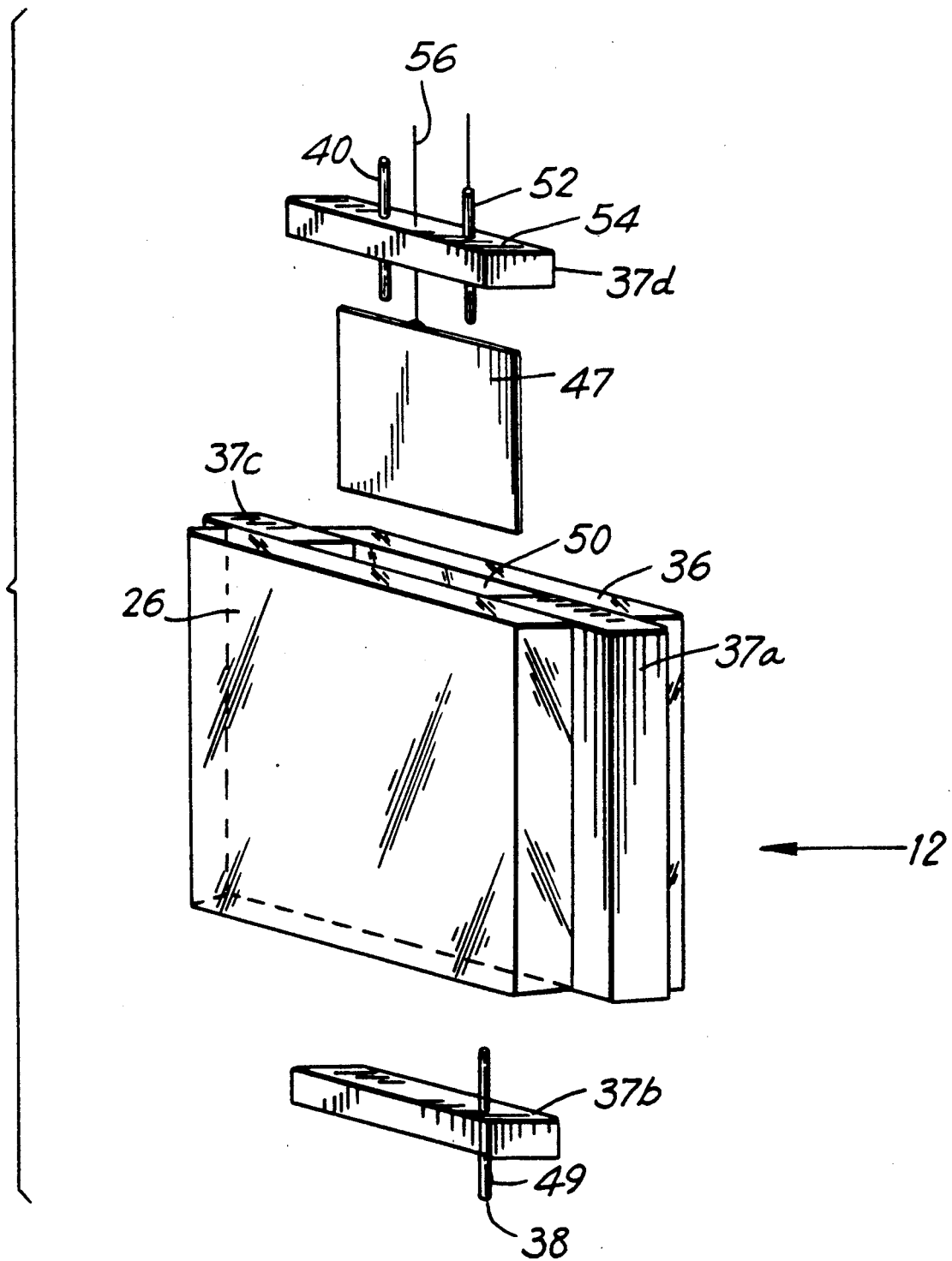
FIG. 4B is an exploded side perspective view of an alternative cell usable in the embodiment of FIG. 1.

While the interdigitated array of working electrode 44 and counter electrode 46 as shown in FIG. 1 is highly advantageous, other electrode patterns may be used depending on the particular application. FIG. 4A shows one alternative configuration for a working electrode 45, made of a thin, transparent, and conductive layer of a metal or an oxide. When an electrode with this type of configuration is mounted on first plate 26, a counter electrode 51 may be mounted on the same plate 26 surrounding the working electrode 45, or advantageously, may be mounted on the second plate 36. FIG. 4B shows another configuration in which working electrode 47 is not mounted on a side plate of cell 12, but rather is suspended in sample-holding volume 50. Working electrode 47 is advantageously a sheet or mesh of gold, platinum, etc. Counter electrode 49 may then be placed outside of cell 12, upstream or downstream thereof, for example in inlet tube 38. If counter electrode 49 is within sample-holding volume 50, it may be in the form of a wire, mesh or thin transparent conducting oxide film on the inside surface of either of plates 26, 36. In such case, working and counter electrodes 47, 49 must be sized and configured so that they do not touch.

The construction of flow-through cell 12 is advantageously made simple for lower cost. As schematically illustrated in FIG. 5, cell 12' may most simply be constructed from a first plate 26' formed advantageously of glass and bearing a working electrode 44' deposited on the inner surface of glass plate 26' as a thin, transparent and electrically conducting film (example materials are gold, tin oxide, indium tin oxide, platinum etc.). Cell 12' further includes a second plate 36', also advantageously glass, bearing a counter electrode 46' made from oxide, gold or platinum. To create the sample holding volume 50', a teflon or glass spacer 67 may be inserted between the two plates 26', 36' having an inlet port 68 and an outlet port 70 through which the sample fluid may be introduced and removed.

Figure 6:
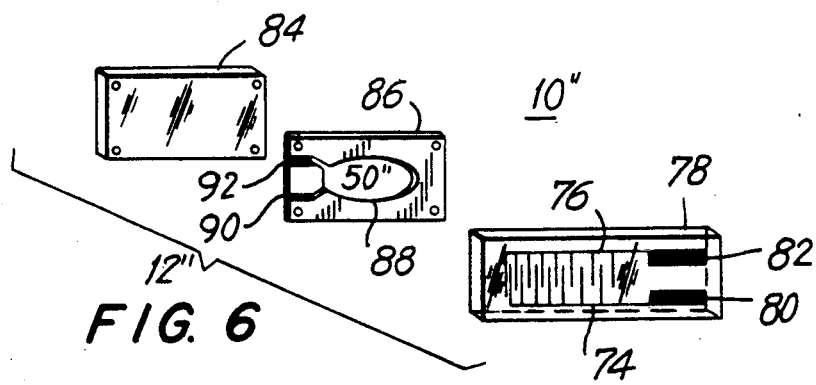
FIG. 6 is an exploded side perspective view of a cell usable in a second embodiment of the apparatus according to the present invention.
Figures 7, 8:
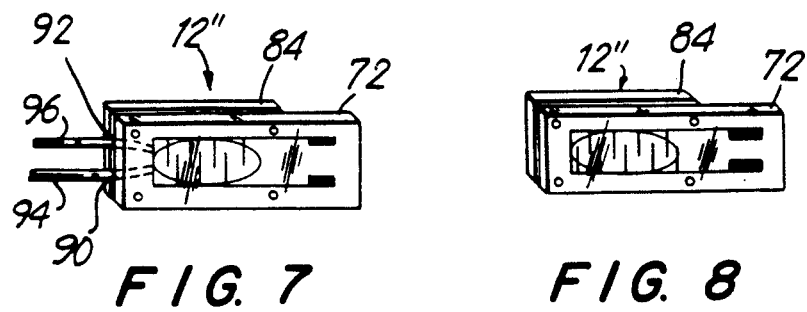
FIG. 7 is a side perspective view of a flow-through cell.
FIG. 8 is a side perspective view of a disposable cell.

Another embodiment of the apparatus 10" according to the present invention is illustrated in FIGS. 6-10. Referring first to FIG. 6, it will be seen that a cell 12" now consists of a first transparent plate 72 bearing an interdigitated array of a working electrode 74 and a counter electrode 76 on an interior surface 78 of plate 72. Working electrode 74 has an electrical contact 80 while counter electrode 76 has an electrical contact 82. A second transparent plate 84 has the same width as first plate 72 but has a shorter length so as to leave contacts 80, 82 exposed when first plate 72 is brought into contact with second plate 84. A thin gasket 86 is provided between the assembled first and second plates 72, 84 that leaves an opening 88 which defines the sample-holding volume 50" and at which working electrode 74 and counter electrode 76 are exposable to the sample. As shown in FIGS. 6 and 7, illustrating an assembled flow-through version of cell 12", gasket 86 may include inlet and outlet holes 90, 92 through which respective tubes 94, 96 may pass to provide an inlet and outlet for the sample. Holes 90, 92 extend through the side of gasket 86 and into opening 88 at the center thereof. Alternatively, the sides of gasket 86 may be solid and, as illustrated in FIG. 8, cell 12" thereupon becomes a "disposable" cell in which the sample is first inserted in sample-holding volume 50" and then plate 72 (or 84) is attached to complete assembly of cell 12". The term "disposable" does not necessarily imply that the cell of FIG. 8 is discarded after each use, but rather that the cell must be removed from the apparatus 10" after each use and a new sample introduced into the sample holding volume 50" therein.

Figure 9:
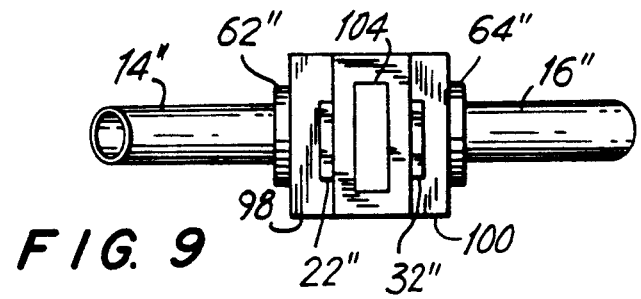
FIG. 9 is a side plan view of the second embodiment of the apparatus according to the present invention.
Figure 10:
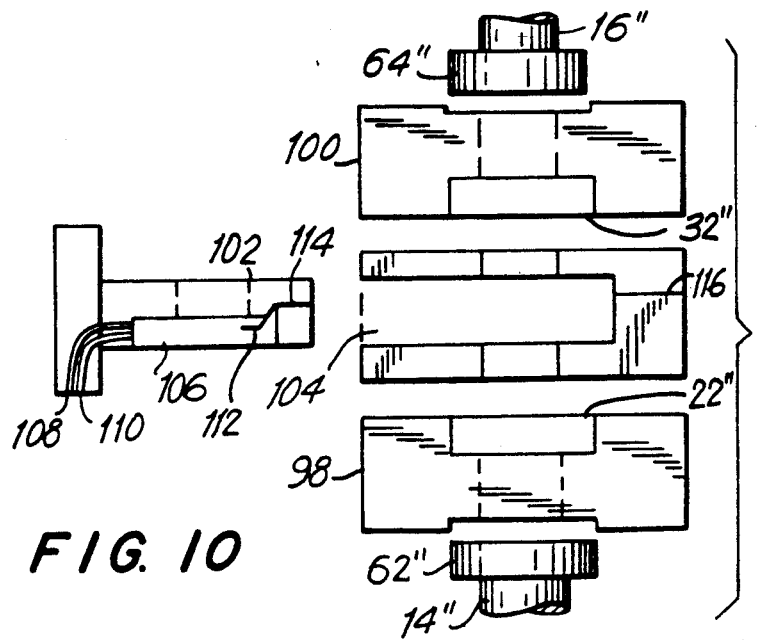
FIG. 10 is an exploded top plan view of the apparatus of FIG. 8 together with a cell of FIG. 5.

FIGS. 9 and 10 are views of the assembled apparatus 10" according to this embodiment. As in the embodiment of FIGS. 1 and 2, apparatus 10" includes a first PMT 14" and an opposing second PMT 16", with respective filters 22", 32" interposed between the PMTs 14", 16" and first and second plates 72, 84. Filter 22" is held in a first filter holder 98, while second filter 32" is held in a second filter holder 100. PMT 14" is connected within the housing by mounting block 62" and PMT 16" is connected within the housing by mounting block 64". Cell 12", whether of the flow-through construction of FIG. 7 or the disposable construction of FIG. 8, is adapted to be held in a cell holder 102 which is slidably received in an access opening 104 of apparatus 10". As shown in FIG. 10, cell holder 102 contains a cell receiving recess 106 and has internal tubing 108, 110 adapted to mate with tubes 94, 96 for providing the inlet and outlet of the sample. An interior electrode surface 112 of recess 106 connects the counter and the working electrodes through an electrical connection 114 which is in turn adapted, when cell holder 102 is within opening 104, to mate with a further electrical connection 116 within apparatus 10" and which in turn leads to voltage control 60 (not illustrated in FIG. 10).

Figure 13:
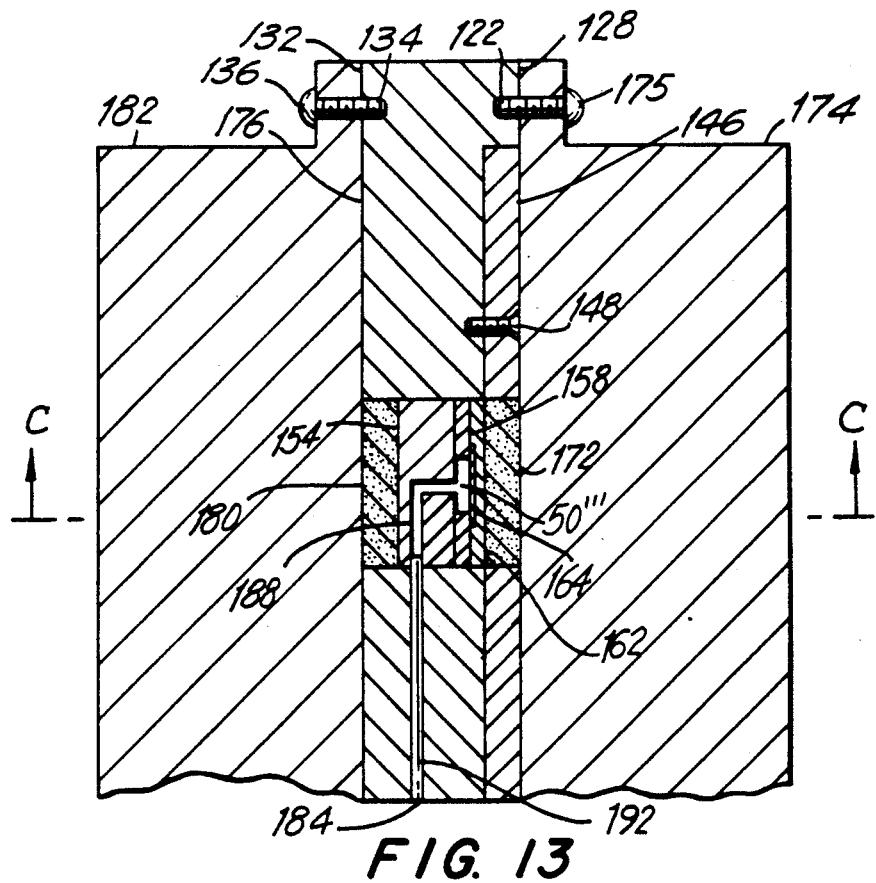
FIG. 13 is an enlarged cross-sectional view taken along line B—B of FIG. 12.

FIGS. 11-14 illustrate a third embodiment of the apparatus 10''' invention. Referring first to FIG. 11, the apparatus 10''' is now basically circular in cross section and includes a mounting block 120 substantially in the form of a disk with a lower portion removed along a line A—A parallel to a diameter of the disk. This configuration is advantageous because many standard optical elements come in circular cross section at a standard radius of three inches with standarized, circularly arranged connections thereon. Therefore, mounting block 120 will advantageously have a matching diameter of three inches and will have three screw receptacles 122, 124 and 126 adapted to match the screw receptacles in conventionally available elements, in particular photomultiplier tubes. Screw receptacles 122-126 are positioned on a facing surface 128 of an outer ring 130. As shown in FIG. 12, a photomultiplier tube (PMT) in a housing 174 may be mounted on ring 130 using screw receptacles 122-126. PMT housing 174 is circular and advantageously has the 3 inch diameter of mounting block 120 and includes, for example, either the R374 or the R1101 PMT produced by Hamamatsu. As shown in FIG. 13, ring 130 has a back facing surface 132 opposed to facing surface 128 with corresponding screw receptacles 134, 136 and 138 for receiving a second PMT housing 182 thereon.

Located radially inside ring 130 is a stepped-down surface 140 which in turn has a plurality of screw receptacles 142 adapted to mate with screw receptacles 144 in a separate mounting plate 146. Mounting plate 146 has a diameter adapted to fit tightly within ring 130 and is held against surface 140 by screws 148. Mounting block 120 and mounting plate 146 are both constructed of an opaque material, advantageously aluminum or stainless steel.

A substantially rectangular recess 150 is centrally located in and extends partially through mounting block 120. A circular aperture 152 is centrally located in recess 150 and extends through the remaining thickness of mounting block 120. Recess 150 fittingly receives a substantially transparent window 154 therein. Window 154 fits into recess 150 and is advantageously made of plexiglas. A Teflon spacer 158 has a central aperture 160 adapted to overlie aperture 152 when spacer 158 is fitted onto window 154. A transparent plate 162 having a working/counter electrode interdigitated array 164 on an inner surface 166 thereof is adapted to be fitted against spacer 158 within recess 150. Wire connections 168, 169 extend from array 164. In apparatus 10''' as assembled, plate 162 is pressed by mounting plate 146 against spacer 158 and thereby depresses spacer 158 against window 154 so as to create a leak proof sample-holding volume 50'''. Electrode array 164 is adapted to overlie aperture 160 so that it will be exposed to any fluid within the sample-holding volume 50''', while wire connections 168, 168 extend from aperture 50''' along surface 140 and out from mounting block 120 so as to be connected to an external potentiostat apparatus.

Sample-holding volume 50''' is advantageously adapted to hold a small volume of sample, advantageously 10-20 microliters. This small volume is advantageous because of the small amount of sample fluid generally available for testing and because, as mentioned above, only the sample fluid immediately surrounding electrode array 164 will emit electrochemiluminescence so that a deeper volume is wasteful and unnecessary and indeed might cause absorption of the emitted light.

Figure 14:
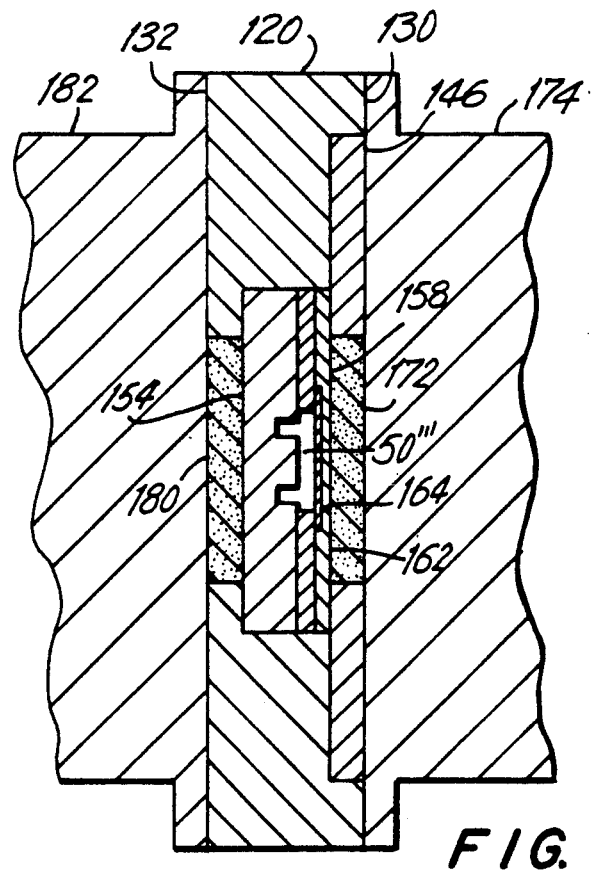
FIG. 14 is a cross-sectional view taken along line C—C of FIG. 13.

Mounting plate 146 has a central aperture 170 which is adapted to overlie apertures 152 and 160. As shown in FIGS. 13 and 14, central aperture 170 is adapted to hold therein a first filter 172 adapted to pass light at the first electrochemiluminescent wavelength 1. First PMT housing 174 (internal structure not illustrated) may then be fitted directly onto mounting plate 146 and be held against mounting block 120 by screws 175 fitting within screw receptacles 122–126 to form a lightproof seal. As further shown in FIGS. 13 and 14, a second filter 180 adapted to pass light at the second electrochemiluminescent wavelength 2 may be fitted into aperture 152 of mounting block 120. A second PMT housing 182 (internal structure not illustrated) may correspondingly be mounted and attached to mounting block 120 via corresponding screws 134 and screw receptacles 136. Thus, light emitted by any sample held within sample-holding volume 50''' and stimulated by electrode array 164 exposed thereto will be emitted both through the partially transparent electrode array 164 on glass plate 162 through first filter 172 to first PMT housing 174 and through the rear surface of plexiglas window 154 to second filter 180 and then to second PMT housing 182. Consequently, the first PMT in housing 174 may be operated to perform an ECL light detection measurement of the prime analyte of interest while the PMT in housing 182 may simultaneously perform an ECL light detection measurement on the internal standard or second analyte of interest. It will be understood, of course, that while the two PMTs in housings 174, 182 may be simultaneously operated as suggested, it is possible to operate only one of them at any particular time, if so desired.

If apparatus 10''' is designed to be operated in the "disposable" mode, window 154 and mounting block 120 may be constructed as described above without further modification. In such case, the sample is inserted within apparatus 10''' by opening up the apparatus, that is, removing PMT 174, mounting plate 146, plate 162 and advantageously spacer 158. The sample may then be manually deposited within the sample-holding volume 50''' and apparatus 10''' reassembled to perform the ECL measurements.

Alternatively and advantageously, however, apparatus 10''' may be constructed as a flow-through instrument. In this case, two holes 184, 186 are drilled through the lower flat surface of housing 120 and up through and into recess 150. Window 154 itself includes two identical backwardly and downwardly extending L-shaped passages 188 (FIG. 13) and 190 (not illustrated). Two tubes, 192, 194, advantageously constructed of stainless steel are passed up through respective holes 184, 186 within mounting block 120 to connect with passages 192, 194, respectively, as best seen in FIG. 13. Tubes 192 and 194 thus hold window 154 in recess 150. Tube 192 serves as an inlet port, while tube 194 serves as an outlet port. Therefore, the sample may be introduced into sample-holding volume 50''' by flowing the sample through tube 192 and out through 194.

It will be seen that this embodiment of the apparatus according to the present invention is advantageous, among other reasons, in that it eliminates the need for a separate, light proof housing, it minimizes the sample-holding volume and it is adapted to receive standard optical elements.

Although the present invention has been described in connection with three preferred embodiments, it will be apparent that many changes and modifications may be made therein without departing from the spirit or scope of the present invention. For example, the present invention is not limited to the use of only two light detectors, but rather, if the sample cell is large enough, two or more light detectors may be positioned adjacent one or both sides of the cell. Alternatively, the cell can have a rectangular or polygonal cross section with working electrodes at least on one of the internal surfaces of the cell and with light detectors positioned abutting two or more of the sides. The sides of the cell themselves need not necessarily be flat but may present curved surfaces. In the "disposable" embodiments, the entire cell, the plate bearing the working electrode or just the working electrode may be discarded and replaced when the working electrode becomes fouled.

Furthermore, each of the light detection devices need not necessarily be operative at the same time, but at least two should be adapted for simultaneous operation so that two simultaneous ECL measurements may be performed if desired. The apparatus may not necessarily be operated in this mode, and may optionally be operated to perform a single ECL measurement or successive ECL measurements at the same or different wavelengths. However, the apparatus according to the present invention retains the option of simultaneous ECL measurements even when operated in different modes.

Many other electrode and cell configurations and constructions are possible and other modifications are also possible, and therefore the scope of the present invention should be determined by reference to the appended claims.

What is claimed is:

1. An apparatus for conducting two simultaneous measurements of electrochemiluminescent phenomena, comprising:
   (a) electrochemical cell means for holding a sample therein, said cell means including a sample-holding volume and first and second transparent plates at least partly defining said sample-holding volume therebetween;
   (b) electrode means including at least a working electrode and a counter electrode for triggering electrochemiluminescence in a sample held within said sample-holding volume, said working electrode being mounted on at least one of said first and second transparent plates so as to be exposable to said sample and further being substantially transparent at a plurality of electrochemiluminescent wavelengths and being configured so as to trigger said sample to emit electrochemiluminescent radiation towards said first and second transparent plates; and
   (c) first light detection means having a light receiving surface confronting said first transparent plate for detecting radiation at a first one of said electrochemiluminescent wavelengths and second light detection means having a light receiving surface confronting said second transparent plate for detecting radiation at a second one of said electrochemiluminescent wavelengths, said first and second light detection means being independently operable and adapted for simultaneous operation for light detection at the first and second wavelengths, respectively.

2. An apparatus according to claim 1, wherein said first and second transparent plates are flat.

3. An apparatus according to claim 2, wherein said first and second transparent plates are opposed to define said sample-holding volume therebetween.

4. An apparatus according to claim 3, wherein said electrode means is configured so as to trigger said sample to emit electrochemiluminescent radiation substantially equally towards said first and second plates.

5. An apparatus according to claim 3, wherein said counter electrode is substantially transparent and said working electrode and said counter electrode are both mounted on said first transparent plate and are each formed as a set of spaced, connected electrodes, the two sets of electrodes being interdigitated to form a substantially transparent interdigitated array on said first transparent plate.

6. An apparatus according to claim 5, wherein each of said sets of electrodes is a set of microelectrodes.

7. An apparatus according to claim 1, wherein each of said first and second light detection means includes a respective filter means at the respective transparent plate, the respective filter means being adapted to transmit light at the respective first and second electrochemiluminescent wavelengths, and detector means for detecting light passed by the respective filter means.

8. An apparatus according to claim 7, wherein said respective filter means are removable from said apparatus.

9. An apparatus according to claim 1, wherein each of said first and second light detection means includes photomultiplier tube means.

10. An apparatus according to claim 1, wherein said working electrode is mounted on said first transparent plate and said counter electrode is substantially transparent and is mounted on said second transparent plate.

11. An apparatus according to claim 1, wherein said working electrode and said counter electrode are both mounted on said first transparent plate.

12. An apparatus according to claim 11, wherein each of said working and counter electrodes is formed as a set of spaced, connected electrodes, the two sets of electrodes being interdigitated to form a partially transparent interdigitated array on said first transparent plate.

13. An apparatus according to claim 12, wherein each of said sets of electrodes is a set of microelectrodes.

14. An apparatus according to claim 1, wherein said cell means is removable from said apparatus and wherein said apparatus further comprises cell holding means for removably holding said cell means at an operative position in said apparatus and fluid transport means for providing a flow of fluid to and from said cell means at said operative position, said cell means being a selected one of a flow-through cell adapted to transfer fluid from and to said fluid transport means and a disposable cell having sample fluid contained therein.

15. An apparatus for conducting a plurality of simultaneous measurements of electrochemiluminescent phenomena comprising:
(a) electrochemical cell means for holding a sample therein, said cell means including a sample-holding volume and first and second transparent plates at least partly defining said sample-holding volume therebetween;
(b) electrode means including at least a working electrode and a counter electrode for triggering electrochemiluminescence in a sample held within said sample-holding volume, said working electrode being mounted on at least one of said first and second transparent plates so as to be exposable to said sample and further being substantially transparent at a plurality of electrochemiluminescent wavelengths and being configured so as to trigger said sample to emit electrochemiluminescent radiation towards said first and second transparent plates; and
(c) a plurality of light detection means having respective light receiving surfaces confronting ones of said first and second transparent plates for detecting light at respective ones of said electrochemiluminescent wavelengths, said plurality of light detection means being independently operable and adapted for simultaneous operation for light detection at the respective wavelengths.

16. An apparatus for conducting a plurality of measurements of electrochemiluminescent phenomena comprising:
(a) electrochemical cell means for holding a sample therein, said cell means including a sample-holding volume;
(b) electrode means including at least a working electrode and a counter electrode for triggering electrochemiluminescence in a sample held within said sample-holding volume, said working electrode being mounted in said sample-holding volume so as to be exposable to said sample;
(c) first and second light detection means for detecting light of at least first and second electrochemiluminescent wavelengths, respectively; and
(d) means interposed between said first and second light detection means and said cell means for transmitting light at said first and second electrochemiluminescent wavelengths from said sample to said light detection means.

17. An apparatus according to claim 16, wherein said first and second light detection means include respective light receiving surfaces and wherein said means for transmitting light includes first and second filter means confronting the respective light receiving surfaces of said first and second light detection means for passing light at said first and second ones of said electrochemiluminescent wavelengths, respectively.

18. An apparatus according to claim 17, wherein said cell means includes a plate which is at least partly transparent and at least one of said filter means confronts said plate to receive light transmitted therethrough.

19. An apparatus for conducting two simultaneous measurements of electrochemiluminescent phenomena, comprising:
(a) electrochemical cell means for holding a sample therein, said cell means including opposed first and second transparent plates defining a sample-holding volume therebetween;
(b) electrode means mounted in said cell means and including at least a working electrode and a counter electrode for triggering electrochemiluminescence in a sample held within said sample-holding volume, said working electrode being mounted on at least one of said first and second transparent plates so as to be exposable to said sample and further being substantially transparent at a plurality of electrochemiluminescent wavelengths and being configured so as to trigger said sample to emit electrochemiluminescent radiation towards said first and second transparent plates;

(c) cell holding means for removably holding said cell means at an operative position within said apparatus;

(d) voltage control means adapted to be electrically connected to said electrode means when said cell means is held at said operative position for applying voltage signals to said electrode means;

(e) first light detection means for detecting light at a first one of said electrochemiluminescent wavelengths, said first light detection means including first filter means having a respective light receiving surface directly confronting said first transparent plate for transmitting light at said first one of said electrochemiluminescent wavelengths and photomultiplier tube means directly confronting said first filter means for detecting light transmitted by the latter; and (f) second light detection means for detecting light at a second one of said electrochemiluminescent wavelengths, said second light detection means including second filter means having a respective light receiving surface directly confronting said second transparent plate for transmitting light at said second one of said electrochemiluminescent wavelengths and second photomultiplier tube means directly confronting said second filter means for detecting light transmitted by the latter;

(g) said first and second light detection means being independently operable, whereby said apparatus is adapted for light detection at the first and second wavelengths by said first and second light detection devices, respectively, to conduct two simultaneous measurements of electrochemiluminescent phenomena.

20. A method for conducting a plurality of simultaneous measurements of electrochemiluminescent phenomena, comprising the steps of:

(a) selecting a sample including at least first and second electrochemiluminescent moieties which are respectively electrochemically inducible to emit light at respective first and second electrochemiluminescent wavelengths;

(b) exposing said sample to a working electrode adapted to induce the emission of light in said sample;

(c) applying a voltage signal to said working electrode to induce the emission of light at said first and second electrochemiluminescent wavelengths;

(d) detecting light at said first electrochemiluminescent wavelength using a first light detection means; and (e) simultaneously detecting light at said second electrochemiluminescent wavelength using a second light detection means.

21. A method for conducting a plurality of measurements of electrochemiluminescent phenomena, comprising the steps of:

(a) selecting a sample including at least first and second electrochemiluminescent moieties which are respectively electrochemically inducible to emit light at respective first and second electrochemiluminescent wavelengths;

(b) exposing said sample to a working electrode adapted to induce the emission of light in said sample;

(c) applying a voltage signal to said working electrode to induce the emission of light at said first and second electrochemiluminescent wavelengths;

(d) detecting light at said first electrochemiluminescent wavelength using a first light detection means; and (e) detecting light at said second electrochemiluminescent wavelength using a second light detection means.

* * * * *